[19] United States Patent
Boghosian et al.

[11] 4,244,948
[45] Jan. 13, 1981

[54] MEDICAL USE OF ESTERS OF ACETYLSALICYLIC ACID TO TREAT ACNE

[75] Inventors: Malcolm P. Boghosian, Long Beach; Robert T. Koda, Anaheim, both of Calif.

[73] Assignee: Allergan Pharmaceuticals, Inc., Irvine, Calif.

[21] Appl. No.: 36,354

[22] Filed: May 7, 1979

[51] Int. Cl.³ ............................................. A61K 31/60
[52] U.S. Cl. .................................................... 424/230
[58] Field of Search .............................. 424/230, 234

[56] References Cited
U.S. PATENT DOCUMENTS
4,126,681  11/1978  Reller .................................. 424/234

Primary Examiner—Stanley J. Friedman
Attorney, Agent, or Firm—Martin A. Voet

[57] ABSTRACT

A method for topically treating inflammation in humans or animals by administering to the inflamed area a therapeutically effective amount of an alkyl- or aralkyl-substituted acetylsalicylic acid such as methyl-, ethyl-, allyl- or benzyl acetylsalicylate. The method may also be used to treat acne by applying a therapeutically effective amount of the acetylsalicylate ester to the affected skin in a human having skin affected by acne.

4 Claims, No Drawings

MEDICAL USE OF ESTERS OF ACETYLSALICYLIC ACID TO TREAT ACNE

BACKGROUND OF THE INVENTION

1. Field of the Invention

The invention relates generally to a method for topically treating inflammation in humans or animals. More particularly, the invention relates to a method of treating inflammation in humans and animals with acetylsalicylic acid esters.

2. Background of the Prior Art

Acetylsalicylic acid or aspirin, as it is commonly known, is well known in the art. Alkyl and aralkyl esters of acetylsalicylic acid also are known in the prior art. For example, methyl acetylsalicylate is disclosed in U.S. Pat. No. 3,119,739 as an anodyne agent useful in alleviating pain associated with insect bites. The Merck Index, 9th ed., discloses that methyl acetylsalicylate also is used as a fixative for perfumes. U.S. Pat. No. 2,113,374 discloses salicylic acid derivatives of polyhydric alcohols useful as topically active analgesics and antirheumatics. U.S. Pat. No. 4,126,681 discloses multiple uses of non-acetylated salicylates in topical preparations for the treatment of inflammation including acne and also discloses a topical composition containing acetylsalicylic acid combined with topical components to enhance penetration of the skin of the acetylsalicylic acid. As discussed in U.S. Pat. No. 4,126,681, the anti-inflammatory response of tissue to acetylsalicylic acid, as well as skin irritating properties of acetylsalicylic acid, has been recognized. However, the delivery of acetylsalicylic acid to the skin in a form which can be readily absorbed by the skin and is not irritating to tissues has not been satisfactorily solved by the prior art.

SUMMARY OF THE INVENTION

It has now been discovered that certain alkyl and aralkyl esters of acetylsalicylic acid easily penetrate the skin when used topically and result in enhanced penetration of the skin of acetylsalicylic acid with decreased irritation to tissues normally associated with topical use of acetylsalicylic acid.

More specifically, the invention relates to a method for topically treating inflammation in humans or animals comprising administering topically to the inflamed area a therapeutically effective amount of an alkyl or aralkyl ester of acetylsalicylic acid, such as, for example, methyl acetylsalicylate, ethyl acetylsalicylate, allyl acetylsalicylate and benzyl acetylsalicylate.

DETAILED DESCRIPTION OF THE INVENTION

Alkyl substituents suitable for combining with the acetylsalicylic acid to produce the subject esters include alkyl groups having 1 to 12 carbon atoms and may be saturated and unsaturated, straight or branched chain or cyclic. Similarly, conventional aralkyl substituents may be used including benzyl and related aralkyl substituents.

Specific esters of acetylsalicylic acid which may be used in the present invention include, for example, methyl acetylsalicylate, ethyl acetylsalicylate, allyl acetylsalicylate, cyclohexyl acetylsalicylate and benzyl acetylsalicylate. Compositions comprising one or more of these esters in therapeutically effective amounts and pharmacologically acceptable carriers are convenient for their administration. The preferred ester is ethyl acetylsalicylate.

Ethyl acetylsalicylate, for example, has a low degree of toxicity to external tissues, such as the skin and eye, and has excellent penetration of these tissues. For example, it penetrates the skin almost quantitatively (80 to 90% of the applied amount can be recovered as typical salicylate metabolites in five (5) days in guinea pigs following topical administration of ethyl acetylsalicylate). Similarly, ethyl acetylsalicylate penetrates acne-affected tissues including the comedone. Ethyl acetylsalicylate also has been shown to exhibit anti-inflammatory activity in a number of areas including uveitis in rabbits, ultraviolet radiation-induced erythema, anti-acne activity in vitro and tetrahydrofurfuryl-induced inflammation in skin.

The aforementioned esters have been found to be therapeutically effective in from about 0.01 to about 20 percent by weight relative to the carrier. Generally, however, amounts from about 0.1 to about 10 percent by weight will provide the desired therapeutic effect and are preferred.

Suitable conventional vehicles or carriers for the topical administration of the aforesaid esters can be any conventional solution, lotion, emulsion, ointment or gel.

Convenient liquid vehicles which are useful in the application of the aforementioned esters are, water, alcohols, such as methanol, ethanol, propanol and isopropanol; water-alcohol solutions; or water-alcohol-polyalkeneglycol solutions. A convenient vehicle for the administration of one or more of the subject esters is a water-ethanol-propylene glycol solution having a weight composition of 50% water, 30% ethanol and 20% propylene glycol.

The compositions of the present invention are useful in treating inflammation of the skin, including acne. For purposes of this disclosure, the term "treatment of acne" is used to mean the temporary alleviation of the inflammation of the affected skin and other signs and symptoms associated with acne.

EXAMPLE

Examples of an ethyl acetylsalicylate-containing (EAS) gel, cream and ointment that are convenient to apply to skin are as follows:

| GEL | |
|---|---|
| Alcohol | 50% to 80% |
| Silicone Fluid (e.g., Dow 556) | up to 10% |
| Hydroxyethyl or hydroxypropyl cellulose | up to 5% |
| EAS | 1% |
| CREAM | |
| Water | 60% to 80% |
| Oleth 3-phosphate | up to 5% |
| Petrolatum | up to 15% |
| Synthetic spermaceti | up to 5% |
| Carboner 934 | up to 5% |
| Benzyl alcohol | up to 3% |
| EAS | 5% |
| OINTMENT | |
| Polyethylene glycol 4000 | 15% to 25% |
| Polyethylene glycol 300 | up to 5% |
| Cetyl steryl glycol | 15% to 25% |
| Isopropyl myristate | 25% to 35% |
| Benzyl alcohol | 1% to 3% |
| Isopropyl or ethyl alcohol | 10% to 25% |
| EAS | 10% |

We claim:

1. A method for treating acne in a human having skin affected thereby comprising administering topically to the affected skin a therapeutically effective amount of an ester of acetylsalicylic acid selected from the group consisting of methyl acetylsalicylate, ethyl acetylsalicylate, allyl acetylsalicylate and benzyl acetylsalicylate.

2. The method of claim 1 where the ester of acetylsalicylic acid is administered as a composition comprising about 0.1 to about 10 percent by weight of said ester in admixture with a pharmaceutically acceptable carrier.

3. The method of claim 2 wherein said composition is in the form selected from the group consisting of a solution, lotion, ointment, emulsion and gel.

4. A method for treating acne in humans comprising administering topically to the affected skin a composition comprising about 0.1% to about 10% by weight of ethyl acetylsalicylate in admixture with a pharmaceutically acceptable carrier.

* * * * *